United States Patent [19]

McCloud

[11] Patent Number: 4,961,736
[45] Date of Patent: Oct. 9, 1990

[54] REUSABLE DIAPER WITH DETACHABLE LINER

[75] Inventor: Debra S. McCloud, Edmonds, Wash.

[73] Assignee: A Better World Company, Edmonds, Wash.

[21] Appl. No.: 487,642

[22] Filed: Mar. 2, 1990

[51] Int. Cl.⁵ .................. A61F 13/15; A61F 13/20
[52] U.S. Cl. .................. 604/385.1; 604/397; 604/398; 604/402
[58] Field of Search .................. 604/385.1, 397, 398, 604/399, 402

[56] References Cited

U.S. PATENT DOCUMENTS

| | | | |
|---|---|---|---|
| D. 249,280 | 9/1978 | Banuelos | D24/50 |
| 1,800,739 | 4/1931 | Marinsky | 604/402 |
| 2,595,507 | 5/1952 | Beck | 604/397 |
| 3,081,772 | 3/1963 | Brooks et al. | 604/397 |
| 3,156,241 | 11/1964 | Hyde et al. | 604/402 |
| 3,359,980 | 12/1967 | Rosenblatt | 604/391 |
| 3,653,381 | 4/1972 | Warnken | 604/391 |
| 3,882,871 | 5/1975 | Taniguchi | 604/372 |
| 3,955,575 | 5/1976 | Okuda | 604/371 |
| 4,402,690 | 9/1983 | Redfern | 604/391 |
| 4,410,327 | 10/1983 | Baggaley | 604/391 |
| 4,568,342 | 2/1986 | Davis | 604/391 |
| 4,680,030 | 7/1987 | Coates et al. | 604/391 |
| 4,681,581 | 7/1987 | Coates | 604/391 |
| 4,704,117 | 11/1987 | Mitchell | 604/391 |
| 4,773,906 | 9/1988 | Krushel | 604/391 |
| 4,801,298 | 1/1989 | Sorenson et al. | 604/384 |

*Primary Examiner*—Randall L. Green
*Assistant Examiner*—Paul Prebilic
*Attorney, Agent, or Firm*—Christensen, O'Connor, Johnson & Kindness

[57] ABSTRACT

A reusable cloth diaper (10) that includes a highly absorbent inner liner (40) permanently attached at one edge (42) to an absorbent panel (12). The opposite edge (44) of the liner (40) is detachably attached to the panel (12). The partially detachable liner (40) facilitates the cleaning and drying of the cloth diaper (10).

19 Claims, 4 Drawing Sheets

REUSABLE DIAPER WITH DETACHABLE LINER

FIELD OF THE INVENTION

The present invention relates to diapers, particularly a reusable primarily cloth diaper suitable for use on babies and young children.

BACKGROUND OF THE INVENTION

Disposable and reusable diapers are both commonly used on young children and babies. Disposable diapers generally include a thin inner liner that is normally not absorbent and serves to conform to the shape of the wearer, an outer water impervious layer and an absorbent core sandwiched between the inner liner and the outer layer. Disposable diapers have been well received by mothers and fathers primarily because of their convenience and disposability. However, the number of diapers used by a typical baby during one day creates a large volume of garbage and a serious sanitation problem since most parents do not remove the feces from the diaper before disposing of the diaper. In addition, disposable diapers are relatively expensive. With the growing concerns for the environment, parents are looking to alternative diapers that are reusable, as well as less expensive.

Reusable cloth diapers have been designed attempting to incorporate some of the desirable characteristics of disposable diapers such as water impervious outer layers, highly absorbent liners and adjustable fasteners for a "one-size-fits-all" type of diaper. However, heretofore reusable cloth diapers have suffered from drawbacks that have limited their desirability among many parents.

For example, in order to approach the absorbence capacity of disposable diapers, that often use synthetic polymers to increase the absorbence capacity of the core, reusable cloth diapers require the use of multiple layers of woven cotton. As the number of layers increases, the time required to dry the diaper after laundering increases. If the diapers are hung to dry, the increased time is inconvenient and may require the purchase of extra diapers to maintain an adequate supply of clean, dry diapers. If the diapers are machine dried, longer drying times are required which translates into increased energy costs.

Another problem with cloth diapers arises when the feces is removed from the diaper by dipping it in a toilet. With cloth diapers, this causes the entire portion of the diaper dipped in the toilet to become wet. These wet diapers are messy and cumbersome to handle. Also, when stored prior to laundering, these wet portions, compared to the dry portions, are more susceptible to the growth of microorganisms.

SUMMARY OF THE INVENTION

The present invention relates to a reusable diaper that includes a partially detachable absorbent liner that makes the cleaning of the diaper in a toilet less cumbersome than other diapers. The partially detachable liner also allows the diaper to be dried in a shorter period of time compared to diapers of similar weight without a partially detachable liner because a larger surface area of the diaper is exposed for air to circulate around. Since the partially detached liner can be dipped into a toilet without dipping the other portions of the diaper, only the liner gets wet which reduces the size of the moist portions of the diaper where bacteria tend to grow. The diapers formed in accordance with the present invention are reusable and can be repeatedly machine washed. Economically, the diapers are less expensive to use than disposable diapers or diapers provided by commercial diaper services.

BRIEF DESCRIPTION OF THE DRAWINGS

The present invention will be described in greater detail with reference to the accompanying drawings, which illustrate a preferred embodiment of the invention, wherein.

DETAILED DESCRIPTION OF THE INVENTION

Figures 1, 2:
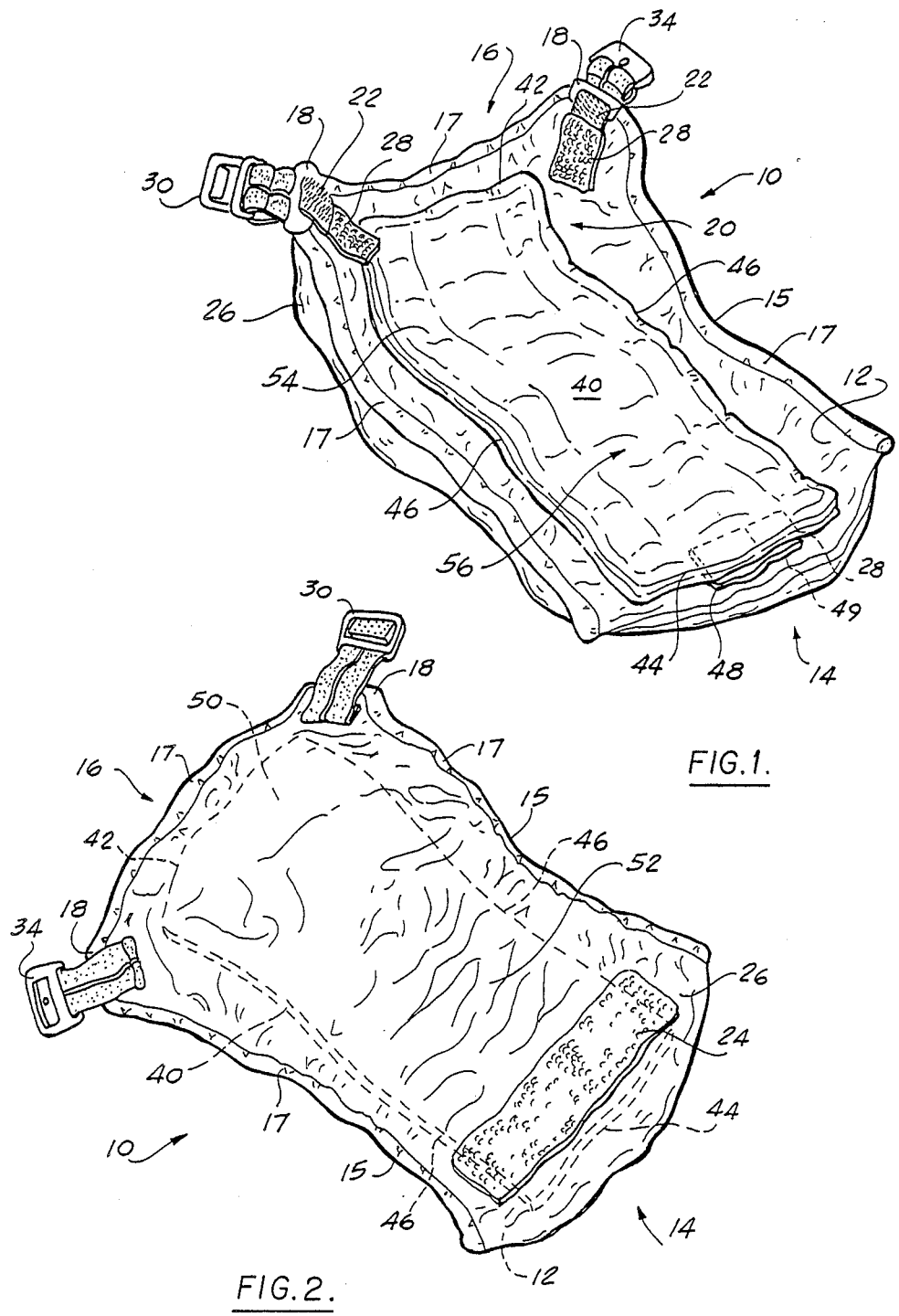
FIG. 1 is a perspective view of the inside of an unfolded diaper formed in accordance with the present invention.
FIG. 2 is a perspective view of the outside of the unfolded diaper in FIG. 1.

Referring to FIG. 1, the diaper generally represented by reference numeral 10 formed in accordance with the present invention includes a panel 12 having on one end a wide front portion 14 and at the opposite end a wide back portion 16. It is preferred that panel 12 comprise a material that absorbs fluids such as urine; however, non-absorbent material can be used. Absorbent panel 12 is preferably composed of a weave of cotton commonly known as birdseye cotton. Also preferably, two layers of birdseye cotton make up absorbent panel 12. One source of birdseye cotton is Dundee Mills in Hartwell, Ga. Absorbent panel 12 also includes arcuate cutouts 15 for receiving the baby's legs when the diaper is placed on the baby. An elastic trim 17 is sewn along the marginal length of absorbent panel 12 corresponding to cutouts 15. The trim enables the arcuate cutouts 15 to expand and return to their original length so that the cutouts 15 fit snugly around the legs of the baby. Elastic trim 17 is also provided along wide back portion 14 between tab 18 to help secure the waist of diaper 10 around the baby.

Two tabs 18 extend outward from each side of wide back portion 16. The inner surface of each tab 18 includes a fastener 22 that can be a strip of hook type or loop type fastener sold under the trademark VELCRO TM. Depending on whether fastener 22 includes a strip of the hook type or loop type fastener, a counterpart type of fastener 24 is mounted on the outside, wide front portion 14 of the diaper. In other words, if fastener 22 is a hook type fastener, fastener 24 would be a loop type fastener and vice versa. Fastener 24 is an elongate strip extending across substantially the entire width of wide front portion 14. By providing a strip that extends across the width of wide front portion 14, the waist of diaper 10 can be adjusted to different lengths by selective positioning of fasteners 22 on fastener 24. When fasteners 22 are of the hook type, they also include a cover 28 in the form of a strip of loop type fastener material. When fasteners 22 are detached from fastener means 24, covers 28 can be placed over the hook type fasteners 22 to prevent the fasteners 22 from attaching to the panel 12 and to protect them from collecting lint or other small pieces of cloth during laundering and machine drying.

Attached to the free end of one tab 18 is a male half 30 of a buckle 32. On the free end of the other tab 18 is a female half 34 of buckle 32. Buckle 32 serves as a secondary fastener for securing diaper 10 around the waist of the baby. Preferably, buckle 32 is made of plastic and cannot be released by a baby or small child. Such buckles are common articles of commerce.

Still referring to FIG. 1, centrally positioned on the inner surface 20 of absorbent panel 12 is a rectangular, partially detachable absorbent liner 40. In FIG. 1, end edge 42 of absorbent liner 40 is fixed to the inner surface 20 of wide back portion 16, for instance by stitching. The opposite end of detachable absorbent liner 40 includes an end edge 44 that is detachably attachable to the inner surface 20 of wide front portion 14. The two elongated side edges 46 of detachable absorbent liner 40 are not fastened to the inner surface 20 of absorbent panel 12.

Detachable end edge 44 of absorbent liner 40 is attachable to wide front portion 14 by (1) a strip 48 of hook type or loop type fastener sewn onto the unexposed surface 50 of absorbent liner 40 and (2) a counterpart strip 49 of either hook type or loop type fastener sewn onto the inner surface 20 of absorbent panel 40. The strip 48 is positioned at a distance apart from fixed end edge 42 such that when laid flat, the attached absorbent liner 40 lies substantially flat on absorbent panel 12. When strip 48 or 49 is a hook type fastener, it includes a cover means 28 in FIG. 3 of a loop type fastener for preventing strip 48 or 49 from attaching to absorbent panel 12 and to protect them from collecting lint or other small pieces of cloth during laundering and machine drying.

Figure 5:
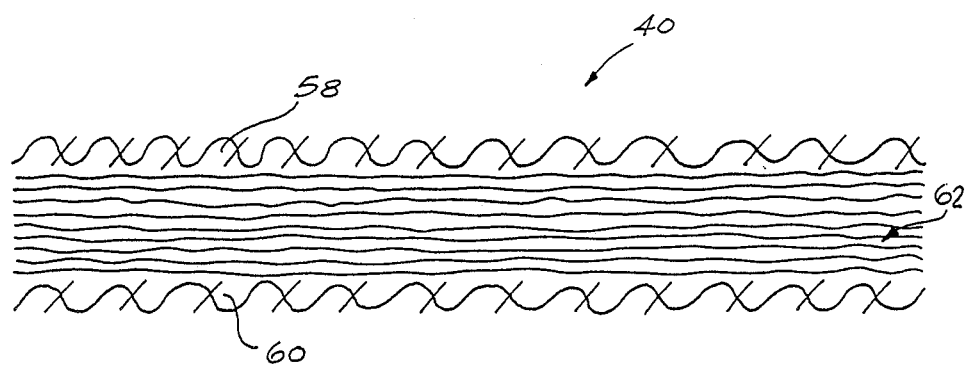
FIG. 5 is a side view of an absorbent liner formed in accordance with the present invention with a portion cut away.

Partially detachable liner 40 preferably includes two layers 58 and 60 of preshrunk birdseye cotton that sandwiches therebetween from about eight to ten layers 62 of unshrunk cotton gauze. Unshrunk cotton gauze is used so that when washed and dried, the layers 62 of cotton gauze will shrink, giving the composite construction of absorbent liner 40 a quilted interior as shown in FIG. 5. The quilting of the interior of absorbent liner 40 is preferred because it improves the absorbency of the liner as well as increases the ability of drying air to circulate around and through wet portions of the liner. The edges of the two layers 58 and 60 of birdseye cotton and layers 62 of cotton gauze are fastened together around the edges for example by stitching. If stitching is used, the stitching should be provided on the inside of the liner where it will not rub against the baby's skin.

It should be understood that although the detachable absorbent liner 40 in FIG. 1 is illustrated as having a rectangular shape, other shapes of liners such as ovals can also be used.

Referring to FIG. 2, the outer surface 52 of diaper 10 includes a water impervious outer layer 26 preferably composed of plastic or vinyl. Optionally, a layer of nylon taffeta can be provided over the plastic or vinyl layer for aesthetic purposes and to protect the water impervious plastic or vinyl layer from damage such as tearing. Absorbent panel 12, water impervious vinyl layer 26 and optional nylon taffeta layer are all stitched to the elastic trim 17 along the length of the arcuate cutouts 15 and along a middle portion of wide back portion 16. In addition, the outer edges of panel 12 and water impervious layer 26 are stitched together. Outer surface 52 of diaper 10 also includes a strip of hook type or loop type fastener means 24 along wide front portion 14 as described above with reference to FIG. 1.

Figure 3:
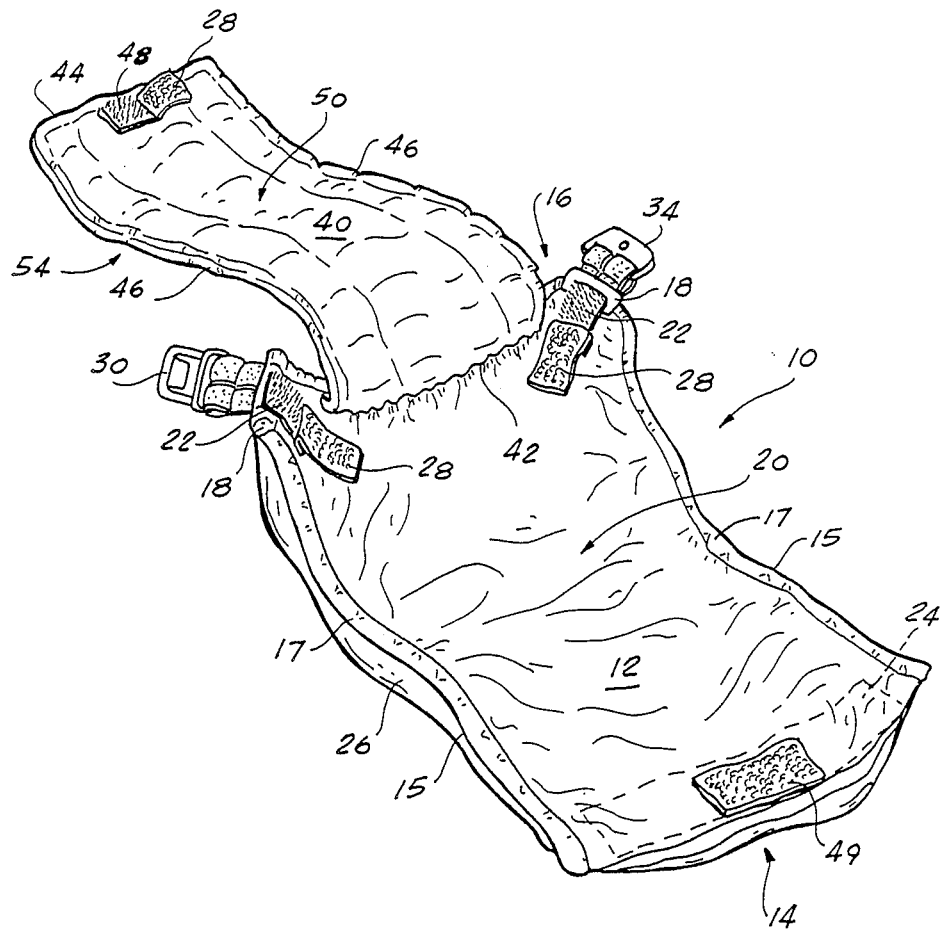
FIG. 3 is a perspective view of an unfolded diaper with the partially detachable liner unfastened in accordance with the present invention.

Referring to FIG. 3, when end edge 44 is detached, absorbent liner 40 can be spaced apart from absorbent panel 12. When this is done, air circulates easily around unexposed surface 50 of liner 40, exposed surface 54 of liner 40 and the portion of absorbent panel 12 that lies under liner 40 when it is not detached. The increased circulation of air decreases the period of time needed to dry the diaper compared to diapers of similar weight that do not have detachable liners.

In use, the free end edge 44 of the detachable liner 40 is desirably coupled to absorbent panel 12 so that absorbent liner 40 does not fall or slide down below the source of urine, particularly when the diaper is worn by a boy. After a bowel movement, the diaper is removed from the baby and end edge 44 of absorbent liner 40 is detached from absorbent panel 12. The hanging liner 40 and other soiled portions of the diaper are then easily dipped into a toilet without having to get the rest of the diaper wet.

Figure 4:
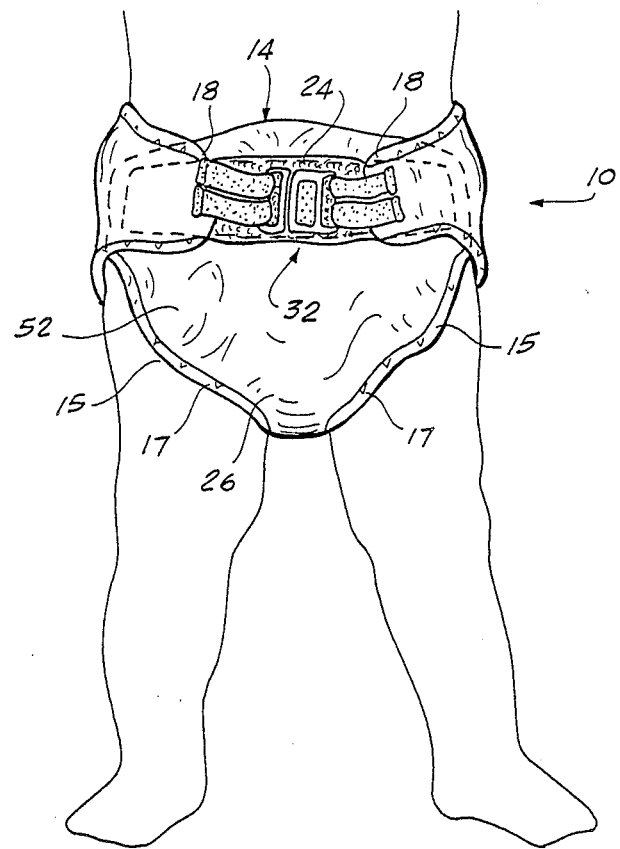
FIG. 4 is a perspective view of a diaper formed in accordance with the present invention in a folded use position.

Referring to FIGS. 1 and 4, diaper 10 is placed on the baby by securing the free end edge 44 of the absorbent liner 40 to absorbent panel 12 and then positioning the baby's bottom on the center portion 56 of detachable absorbent liner 40. The baby should be facing wide front portion 14. Front portion 14 is then brought up between the baby's legs while at the same time bringing tabs 18 up around the back of the baby to his front so that fasteners 22 can be attached to fastener 24. Fasteners 22 should be adjusted along the length of fastener 24 so the waist of diaper 10 fits snugly around the baby. Also, buckle 32 should be fastened to ensure the baby does not remove the diaper.

It should be understood that, while a preferred embodiment of the present invention has been illustrated and described, various changes can be made therein without departing from the spirit and scope of the invention. For instance, detachable end edge 44 and fixed end edge 42 of absorbent liner 40 could be reversed although doing so is not preferred from the standpoint of placing the diaper on the baby. Other combinations and numbers of cotton layers can also be used if different degrees of absorbency are desired. Fasteners other than hook type and loop type fasteners could be used.

The embodiments of the invention in which an exclusive property or privilege is claimed are defined as follows:

1. A reusable diaper comprising:
   a panel having a front end, a back end, an inner surface and an outer surface;
   tab means extending outward from each side of the back end, the tab means having an inner surface and an outer surface;
   fastener means on the inner surface of each tab means and on the outer surface of the front end;
   an absorbent liner having a fixed edge permanently attached to one end of the panel, a detachable edge opposite the fixed edge, two sides unattached to the panel, an exposed surface nominally facing away from the panel and an unexposed surface nominally facing toward the panel; and
   detachable coupling means on the unexposed surface of the liner adjacent the detachable edge thereof and on the inner surface of the panel for detachably coupling the detachable edge of the liner to the panel.

2. The reusable diaper of claim 1, wherein the fixed edge of the liner is fixedly attached to the inner surface of the front end of the panel.

3. The reusable diaper of claim 2, wherein the detachable edge of the liner is detachably coupled to the inner surface of the back end of the panel.

4. The reusable diaper of claim 1, wherein the fixed edge of the liner is fixedly attached to the inner surface of the back end of the panel.

5. The reusable diaper of claim 4, wherein the detachable edge of the liner is detachably coupled to the inner surface of the front end of the panel.

6. The reusable diaper of claim 1, wherein the fastener means on the inner surface of the tab means includes hook means and the fastener means on the outer surface of the front end includes loop means.

7. The reusable diaper of claim 6, wherein the fastener means on the inner surface of the tab means includes a cover means for overlying the hook means when it is unfastened from the loop means.

8. The reusable diaper of claim 1, wherein the fastener means on the inner surface of the tab means includes loop means and the fastener means on the outer surface of the front end includes hook means.

9. The reusable diaper of claim 8, wherein said fastener means on the outer surface of the front end includes a cover means for protecting the hook means when it is unfastened from the loop means.

10. The reusable diaper of claim 1, wherein the detachable coupling means on the inner surface of the panel includes loop means and the detachable coupling means on the unexposed surface adjacent the detachable edge includes hook means.

11. The reusable diaper of claim 10, wherein the detachable coupling means on the unexposed surface includes cover means for overlying the hook means when it is unfastened from the loop means.

12. The reusable diaper of claim 1, wherein the detachable coupling means on the inner surface of the panel includes hook means and the reversible coupling means on the unexposed surface adjacent the detachable edge includes loop means.

13. The reusable diaper of claim 12, wherein the detachable coupling means on the inner surface of the panel includes cover means for overlying the hook means when it is fastened from the loop means.

14. The reusable diaper of claim 1, wherein the liner includes a plurality of layers of unshrunk cotton gauze sandwiched between two layers of woven preshrunk cotton.

15. The reusable diaper of claim 1, further comprising a buckle for securing one tab means to the other tab means when the diaper is folded for use.

16. The reusable diaper of claim 1, wherein the panel absorbs fluids.

17. The reusable diaper of claim 1, further comprising a water impervious layer attached to the outer surface of the panel.

18. The reusable diaper of claim 17, wherein the water impervious layer is sandwiched between the panel and an outer protective covering.

19. A reusable diaper comprising:
an absorbent panel having a front end, a back end, an inner surface and an outer surface;
tab means extending outward from each side of said back end, the tab means an inner surface and an outer surface;
water impervious means on the outer surface of the panel, the water impervious means having an inner surface nominally facing toward the absorbent panel and an outer surface nominally facing away from the absorbent panel;
fastener means on the inner surface of each tab means and on the outer surface of the water impervious means;
an absorbent liner having a fixed edge permanently attached to one end of the absorbent panel, a detachable edge opposite the fixed edge, two sides unattached to the absorbent panel, an exposed surface nominally facing away from the absorbent panel and an unexposed surface nominally facing toward the absorbent panel; and
detachable coupling means on the unexposed surface of the liner adjacent the detachable edge thereof and on the inner surface of the absorbent panel for detachably coupling the detachable edge of the liner to the absorbent panel.

* * * * *

UNITED STATES PATENT AND TRADEMARK OFFICE
CERTIFICATE OF CORRECTION

PATENT NO. : 4,961,736

DATED : October 9, 1990

INVENTOR(S) : Debra S. McCloud

It is certified that error appears in the above-identified patent and that said Letters Patent is hereby corrected as shown below:

| COLUMN | LINE | |
|---|---|---|
| 6 | 4 | "fastened" should be --unfastened-- |

Signed and Sealed this

Seventeenth Day of March, 1992

Attest:

HARRY F. MANBECK, JR.

*Attesting Officer*      *Commissioner of Patents and Trademarks*